US007801689B2

(12) United States Patent
Roy et al.

(10) Patent No.: US 7,801,689 B2

(45) Date of Patent: Sep. 21, 2010

(54) SYSTEMS AND METHODS FOR TRACKING THE COMPOSITION OF DISTILLED SPIRITS IN PRODUCTION AND STORAGE

(75) Inventors: Charu Roy, Saratoga, CA (US); Vinay Ambekar, Saratoga, CA (US); Anjali Kataria, San Carlos, CA (US)

(73) Assignee: Oracle International Corporation, Redwood Shores, CA (US)

( * ) Notice: Subject to any disclaimer, the term of this patent is extended or adjusted under 35 U.S.C. 154(b) by 0 days.

(21) Appl. No.: 11/824,812

(22) Filed: Jul. 3, 2007

(65) Prior Publication Data

US 2008/0091291 A1 Apr. 17, 2008

Related U.S. Application Data

(60) Provisional application No. 60/831,741, filed on Jul. 17, 2006.

(51) Int. Cl.
*G06Q 40/00* (2006.01)
*G01N 31/00* (2006.01)

(52) U.S. Cl. .......................................... 702/27; 705/22

(58) Field of Classification Search .................. 702/27, 702/30–32, 130, 155–156; 705/22, 28–29, 705/413; 707/102, 104.1

See application file for complete search history.

(56) References Cited

U.S. PATENT DOCUMENTS

| | | | | |
|---|---|---|---|---|
| 3,896,659 | A * | 7/1975 | Goodman | 73/19.02 |
| 5,831,859 | A | 11/1998 | Medeiros et al. | |
| 5,847,957 | A | 12/1998 | Cohen et al. | |
| 6,243,615 | B1 | 6/2001 | Neway et al. | |
| 6,458,595 | B1 * | 10/2002 | Selinfreund | 436/20 |
| 6,741,998 | B2 | 5/2004 | Ruth et al. | |
| 6,853,920 | B2 | 2/2005 | Hsiung et al. | |
| 6,865,509 | B1 | 3/2005 | Hsiung et al. | |
| 6,873,914 | B2 | 3/2005 | Winfield et al. | |
| 6,904,370 | B1 | 6/2005 | Levinson et al. | |
| 6,917,845 | B2 | 7/2005 | Hsiung et al. | |
| 6,947,866 | B2 | 9/2005 | Staab | |

(Continued)

FOREIGN PATENT DOCUMENTS

EP 0 612 039 A3 2/1994

(Continued)

*Primary Examiner*—Hal D Wachsman
*Assistant Examiner*—Mary C O'Malley
(74) *Attorney, Agent, or Firm*—Townsend and Townsend and Crew LLP

(57) ABSTRACT

Systems, methods, and apparatus for propagating distilled spirit composition throughout production are disclosed. The composition of distilled spirits in each of a plurality of containers is tracked. A first distilled spirit from a first container in the plurality of containers is blended with a second distilled spirit from a second container in the plurality of containers to form a third quantity of a third distilled spirit. The third distilled spirit is placed into a third container in the plurality of containers and the composition of distilled spirits in the third container is computed based on the known composition and quantities of the first distilled spirit, the second distilled spirit, and the known composition and quantities already present in third container at a time prior to placing the first and second quantities into the third container. The composition and quantity of distilled spirits in the containers is then stored.

46 Claims, 2 Drawing Sheets

Wide area network 34
10
Power Source 24
CPU 22
Communications Circuitry 20
30
36
Operating system 40
File system 42
Spirit process application 44
Dump & batch record & lab test management module 46
Equipment & distillery management module 48
Material management module 50
Inventory tracking module 52
Contract and schedule processing module 54
Source documents and traceability module 56
Composition and brand management module 58
Compliance and regulation management module 60
Common platform module (PCM) 62
Storage database 64
32
26
28
12
Controller
14

U.S. PATENT DOCUMENTS

| | | | | |
|---|---|---|---|---|
| 6,985,779 | B2 | 1/2006 | Hsiung et al. | |
| 6,988,109 | B2 | 1/2006 | Stanley et al. | |
| 7,031,778 | B2 | 4/2006 | Hsiung et al. | |
| 7,123,978 | B2 | 10/2006 | Hartman et al. | |
| 7,131,069 | B1 | 10/2006 | Rush et al. | |
| 7,174,230 | B2 | 2/2007 | Arackaparambil et al. | |
| 7,206,646 | B2 | 4/2007 | Nixon et al. | |
| 2002/0111888 | A1* | 8/2002 | Stanley et al. | 705/31 |
| 2002/0123957 | A1* | 9/2002 | Notarius et al. | 705/37 |
| 2003/0004608 | A1* | 1/2003 | O'Dougherty et al. | 700/244 |
| 2003/0141358 | A1* | 7/2003 | Hudson et al. | 235/375 |
| 2004/0186795 | A1* | 9/2004 | Taylor, Sr. et al. | 705/29 |
| 2004/0190369 | A1* | 9/2004 | Cosman et al. | 366/152.1 |
| 2004/0236463 | A1* | 11/2004 | Weselak et al. | 700/214 |
| 2005/0067425 | A1* | 3/2005 | Bartholomew et al. | 221/119 |
| 2005/0158798 | A1* | 7/2005 | Sher | 435/7.1 |
| 2005/0160077 | A1* | 7/2005 | Howes | 707/2 |
| 2005/0237213 | A1* | 10/2005 | Teller | 340/686.1 |

FOREIGN PATENT DOCUMENTS

| | | | |
|---|---|---|---|
| EP | 0 965 897 | A1 | 12/1999 |
| GB | 2 347 234 | A | 2/2000 |
| WO | WO 03/075206 | A2 | 9/2003 |

* cited by examiner

SYSTEMS AND METHODS FOR TRACKING THE COMPOSITION OF DISTILLED SPIRITS IN PRODUCTION AND STORAGE

CROSS-REFERENCE TO RELATED APPLICATION

This application claims benefit, under 35 U.S.C. §119(e), of U.S. Provisional Patent Application No. 60/831,741, filed on Jul. 17, 2006 which is incorporated herein, by reference, in its entirety.

1. FIELD OF THE INVENTION

The field of this invention relates to computer systems and methods for tracking the composition and age of spirits, spirituous liquor and distilled spirits during production and storage.

2. BACKGROUND OF THE INVENTION

The distilled spirits industry is highly regulated. Spirits, spirituous liquor, and distilled spirits (hereinafter "distilled spirits") are those substances known as ethyl alcohol, ethanol, or spirits of wine in any form, including all such dilutions and mixtures, from whatever source or by whatever process produced, but not denatured spirits unless specifically stated. Examples of distilled spirits include, but are not limited to, rum, scotch, whisky, brandy, bourbon whisky, eau de vie, tequila, vodka, liquors, and the like. Unless falling under an exception, distilled spirits are gauged and the quantities of such spirits must be reported to the Alcohol Tobacco Tax and Trade Bureau (TTB) on a periodic basis. In fact, quantities and amounts of ethanol in distilled spirits should be tracked throughout the distilled spirits production process and any losses of ethanol, due to evaporation or other events, must be noted. Such tasks are complicated by the fact that many commercial distilled spirit products are complex blends of several component distilled spirits of varying age, quality, and composition. In fact, distilled spirits are typically a complex blends of chemicals, filters, additives, and raw materials (e.g. grains, grapes). The final distilled spirits are gauged and quantified in order to account for all ethanol produced and processed, and in order to compute taxes owed to the government on the final product. Permissible procedures are exacting. Moreover, processes for propagating the amounts and volumes of ethanol in distilled spirit production are manually accomplished. This manual process is time consuming and subject to error. Thus, there is a risk that discrepancies in the amount of ethanol that should be present in a final distilled spirit and the amount that is actually present in the distilled spirits cannot be reconciled.

Permissible procedures for gauging and determining quantity of distilled spirits are complex and are set forth in, for example, 27 Code of Federal Regulations (C.F.R.) §30.1 in the United States and comparable laws in other countries. Here, the term "gauging" means the determination of the proof and the quantity of distilled spirits. Such procedures are designed to gauge the distilled spirits for tax purposes. Such procedures can also be used throughout the production process in order to track losses of ethanol due to evaporation and to more accurately propagate composition through the various blends that an inherent component of the process. For instance, United States law states that, hydrometers used to gauge distilled spirits for tax purposes, shall be determined to the nearest tenth degree which shall be the proof used in determining the proof gallons and all fractional parts thereof to the nearest tenth proof gallon. The hydrometers used are graduated to read the proof of aqueous alcoholic solutions at 60 degrees Fahrenheit. Thus, they read, 0 for water, 100 for proof spirits, and 200 for absolute alcohol. Because of temperature-density relationships and the selection of 60 degrees Fahrenheit for reporting proof to the TTB, the hydrometer readings are less than the true percent of proof at temperatures below 60 degrees Fahrenheit and greater than the true percent of proof at temperatures above 60 degrees Fahrenheit. Corrections are necessary for hydrometer readings at temperatures other than 60 degrees Fahrenheit. Such correction factors are promulgated by the TTB in a publication known as the Gauging Manual (ATF publication number ATF-P 5110.6 (November 1978)), which is hereby incorporated by reference herein in its entirety. In the present art, such correction factors are manually obtained from copies of the TTB tables and the correction factors are manually applied to actual measurements made of the distilled spirits or precursors to distilled spirits.

The TTB advises that, in order to obtain accurate readings, bulk spirits are thoroughly agitated so that the test samples will be representative of the entire quantity. Immediately before readings are taken, the glass cylinder containing the thermometer is rinsed several times with the spirits which are to be gauged so as to bring both the cylinder and the thermometer to the temperature of the spirits. If the outer surface of the cylinder becomes wet, it is wiped dry to avoid the cooling effect of rapid evaporation. During the readings the cylinder is protected from drafts or other conditions which might affect its temperature or that of the spirits which it contains. The hydrometer is inserted in the liquid and the hydrometer bulb raised and lowered from top to bottom 5 or 6 times to obtain an even temperature distribution over its surface, and, while the hydrometer bulb remains in the liquid, the stem is dried and the hydrometer allowed to come to rest without wetting more than a few tenths degrees of the exposed stem. The exact point at which the level of the surface liquid intersects the scale of proof in the stem of the hydrometer is determined. The hydrometer and thermometer are immediately read, as nearly simultaneously as possible. In reading the hydrometer, a sighting is made slightly below the plane of the surface of the liquid and the line of sight is then raised slowly until the appearance of the surface changes from an ellipse to a straight line. When the correct readings of the hydrometer and the thermometer have been determined, the true percent of proof is ascertained from Table 1 of the TTB gauging manual. Table 1 provides the true percent of proof a distilled spirit for any indication of the hydrometer at temperatures between zero and 100 degrees Fahrenheit. Typically, another sample of the spirits is then taken and tested in the same manner so as to verify the original measurement.

To illustrate the use of correction factors, consider the case in which a hydrometer reads 192.85° at 72.10° F. The correction factors for the hydrometer and the thermometer, respectively are minus 0.03° and plus 0.05°. The corrected reading, then, is 192.82° at 72.15° F.

193.0° at 72.0° F.=190.2°

192.0° at 72.0° F.=189.1°

Difference=1.1°

192.0° at 72.0° F.=189.1°

192.0° at 73.0° F.=188.9°

Difference=0.2°

The hydrometer difference (1.1°) multiplied by the fractional degree of the hydrometer reading (0.82°)=0.902. The temperature difference (0.2°) multiplied by the fractional degree of the temperature reading (0.15°)=0.03°.

Proof at 60° F.=189.1+0.902−0.03=189.972°=190.0°.

As shown, the final proof is rounded to the nearest tenth of a degree of proof. In such cases, if the hundredths decimal is less than five, it will be dropped; if it is five or over, a unit will be added. As is readily apparent, this correction process is complex and requires several manual computations and consultation of TTB look-up tables.

Distilled spirits may also be gauged using specific gravity hydrometers. Because of temperature density relationships and the selection of the standardization temperature of 60°/60° F. in the United States, specific gravity readings will be greater at temperatures below 60 degrees Fahrenheit and less at temperatures above 60 degrees Fahrenheit. Therefore, correction of the specific gravity readings is necessary for temperatures other than 60 degrees Fahrenheit. Such correction may be ascertained by dividing the specific gravity hydrometer reading by the applicable correction factor in Table 7 of the TTB Gauging Manual. For example, consider the case in which the specific gravity hydrometer reading is 1.1525, the thermometer reading is 68 degrees Fahrenheit, and the true proof of the spirits is 115 degrees. The correct specific gravity reading will be ascertained as follows:

(a) From Table 7 of the Gauging manual, the correction factor for 115° proof at 68° F. is 0.996.

(b) 1.1525 divided by 0.996=1.1571, the corrected specific gravity.

As is readily apparent, this correction process is complex and requires several manual computations and consultation of TTB look-up tables.

In order to pay appropriate taxes, distilled spirits may be gauged, in some instances, by weight in bulk quantities. In such instances, the weight can be determined by means of weighing tanks, mounted on accurate scales. Before each use, the scales are balanced at zero load and the spirits are run into the weighing tank and proofed. If the spirits are to be reduced in proof, the spirits are reduced before final determination of the proof. The scales are then brought to a balanced condition and the weight of the spirits is determined by reading the beam to the nearest graduation mark. From the weight and the proof thus ascertained, the quantity of the spirits in proof gallons is determined by reference to Table 4 of the TTB Gauging Manual. However, in the case of spirits which contain solids in excess of 600 milligrams per 100 milliliters, the quantity in proof gallons is determined by first ascertaining the wine gallons per pound of the spirits and multiplying the wine gallons per pound by the weight, in pounds, of the spirits being gauged and by the true proof and dividing the result by 100. A wine gallon is the liquid measure equivalent to the volume of 231 cubic inches.

In order to pay appropriate taxes, spirits distilled spirits may also be gauged, in some instances, by volume. Such measurement are typically made in tanks, by meters or by other devices or methods authorized by an appropriate TTB officer, or such measurement may be made in tank cars or tank trucks if calibration charts for such conveyances are provided and such charts have been accurately prepared, and certified as accurate, by engineers or other persons qualified to calibrate such conveyances. Volumetric measurements in tanks are made in accurately calibrated tanks equipped with suitable measuring devices, where the actual contents can be correctly ascertained. If the temperature of the distilled spirits is other than the standard of 60 degrees Fahrenheit, gallonage determined by volumetric measurements is corrected to the standard temperature by means of Table 7 of the Gauging Manual. When the quantity of spirits, in wine gallons, has been determined by volumetric measurement, the number of proof gallons is obtained by multiplying the wine gallons by the proof of the spirits. A proof gallon is a United States gallon of proof spirits, or the alcoholic equivalent thereof.

Example

Gauge glass reading inches—88.

Wine gallons per inch—48.96.

Temperature ° F.—72.

Proof of spirits—86.8.

Temperature correction factor (Table 7 of the TTB Gauging Manual)—0.995.

48.96 wine gallons.×88=4308.48 wine gallons.

4308.48 wine gallons×0.995=4286.94 wine gallons.

4286.94 wine gallons×0.868=3721.06392=3721.1 proof gallons.

As is readily apparent, this correction process is complex and requires several manual computations and consultation of TTB look-up tables.

From the above background, it is apparent that tracking the composition and age of distilled spirits throughout a production process is complex. Many blends occur, additives are mixed into the distilled spirits at various stages of production, ethanol and other volatiles evaporate, spillage occurs, measurements must be corrected as a function of temperature, volume and/or hydrometer reading, to name of a few of the many events that can make the process of tracking composition and age of distilled spirits during production more complex. Furthermore, the government imposes exacting requirements on the spirit production process, including requiring exact reconciliation between ethanol production and ethanol shipment as well as exacting requirements on gauging final product. In the art, distilled spirit composition, through each of the blends and other processes, is propagated on paper, if at all. This makes the reconciliation between the quantity of ethanol produced and the quantity of ethanol shipped in the final distilled spirit product a laborious and time consuming task. Moreover, such manual processes do not lend themselves to providing a convenient means for predicting the final composition of the distilled spirits and for reporting losses and gains of distilled spirits in both production and storage on a periodic basis as required by the TTB. Thus, what is needed in the art are improved means for propagating distilled spirit composition through the production process and means for predicting the final composition of a distilled spirit at the end of production. What is further needed in the art are improved systems and methods for tracking losses and gains of distilled spirits, both from a storage perspective and a production perspective, on a periodic basis.

3. SUMMARY OF THE INVENTION

The present invention provides systems and methods for tracking the composition and age of a distilled spirit throughout the production processes. In this way, an estimated composition of the final distilled spirits can be computed. In the systems and methods, the estimated composition of distilled spirits is propagated through all the blends and additive addition steps so that the final composition of the distilled spirits is known. Furthermore, the age of the final blend of distilled spirits is automatically computed based on the age of the youngest distilled spirits used in the blend. Corrections on the volume of distilled spirits during production for temperature are made if necessary. Furthermore, ethanol evaporation rates as a function, time, temperature, and proof in various containers are applied to account for loss of ethanol due to evaporation. Throughout the production process, measurements of composition of intermediate stages of the distilled spirits may be made and this information used to improve the accuracy of the estimated final composition of the final product. The systems and methods further provide the advantage of tracking exact quantities of distilled spirits presently in storage and exact quantities that are currently being processed. Thus, the present systems and methods provide a full solution to the deficiencies found in the prior art. Such processes provide a way to more accurately and, in an automated fashion, estimate the final composition of distilled spirits, compute final taxes owed on the distilled spirits, and perform compliance tasks (e.g., reconcile quantities of ethanol produced with quantities of ethanol sold, track losses and gains of distilled spirits in production on a periodic basis, track losses and gains of distilled spirits in storage on a periodic basis, etc.). Furthermore, operational information is provided in real time since work orders are tracked using a novel database and data entry schemes.

One aspect of the present invention provides a computer program product for use in conjunction with a computer system. The computer program product comprises a computer readable storage medium and a computer program mechanism embedded therein. The computer program mechanism is for propagating distilled spirit compositions throughout a production process and comprises instructions for tracking the composition and age of distilled spirits in each of a plurality of containers used in the production of a distilled spirit product. The mechanism further comprises instructions for blending a first quantity of a first distilled spirit from at least a first container in the plurality of containers with a second quantity of a second distilled spirit from at least a second container in the plurality of containers to form a third quantity of a third distilled spirit. The third quantity of the third distilled spirit is placed into at least a third container in the plurality of containers. In some embodiments, the at least third container is the at least first container or the at least second container. In some embodiments, the at least third container is different than the at least first container and the at least second container. The mechanism further comprises instructions for computing the composition of the distilled spirits in the at least third container based on the known composition of the first quantity of the first distilled spirit, the known composition of the second quantity of the second distilled spirit, and the known composition in the third container at a time prior to when the first and second quantities of distilled spirits were placed in the tank. Then the composition, quantity and age of distilled spirits in the at least first container, the at least second container, and the at least third container are stored.

Still another aspect of the invention is a computer comprising a central processing unit and a memory coupled to the central processing unit. The memory stores a module for propagating distilled spirit compositions throughout a production process. The module comprises instructions for (i) tracking the composition of distilled spirits in each of a plurality of containers used in the production of a distilled spirit product, (ii) specifying a blend of a first quantity of a first distilled spirit from at least a first container in the plurality of containers with a second quantity of a second distilled spirit from at least a second container in the plurality of containers to form a third quantity of a third distilled spirit, (iii) specifying the placement of the third quantity of the third distilled spirit into at least a third container in the plurality of containers, (iv) computing the composition of the distilled spirits in the third container based on the known composition of the first quantity of the first distilled spirit, the known composition of the second quantity of the second distilled spirit, and the known composition in the third container at a time prior to the placing step (iii), and (v) storing the composition, quantity and age of distilled spirits in the first container, the second container, and the third container. In some embodiments, the memory stores a database and the storing step comprises storing the composition, quantity and age of distilled spirits in the first container, the second container, and the third container in the database. Representative container types that are within the plurality of containers includes but is not limited to tank, barrel, mill, pot still, cast, storage silo, high column plate still, mash tub, and quashback. In some embodiments, the plurality of containers consists of containers that are all of the same type. In more common embodiments, the plurality of containers comprises containers of multiple different types.

In some embodiments, the module further comprises instructions for (i) receiving a hydrometer reading and a temperature reading of the first tank, the second tank, or the third tank; (ii) computing a true percent proof of the composition in the first tank, the second tank, or the third tank based on the hydrometer reading and the temperature reading; and (iii) updating a composition of the first tank, the second tank, or the third tank based on the true percent proof. In some embodiments, the memory stores a database and the module further comprises storing the updated composition of the first tank, the second tank, or the third tank in the database. In some embodiments, the module further comprising instructions for (i) receiving a measured volume of said first tank, said second tank, or said third tank, (ii) computing a correction of the measured volume, and (iii) updating a composition of the first tank, the second tank, or the third tank based on the correction of the measured volume. In some embodiments, the module further comprises storing the correction of the measured volume in the database. In some embodiments, the computing step comprises accessing a lookup table stored in the memory that corrects volume as a function of true percent proof and temperature.

Distilled spirits in the third container can be any of a broad range of spirits, including but not limited to, whiskey, blended whiskey with neutral spirits, blended whisky with light whiskey, blended light whiskey, imported scotch, imported Canadian whiskey, domestic whiskey distilled at 160 proof and under, domestic whiskey distilled at over 160 proof, brandy distilled at 170 proof and under, brandy distilled at over 170 proof, Puerto Rican rum, Virgin Islands rum, domestic rum, gin, vodka, a cordial, a liquor, and/or tequila, mixtures thereof, precursors thereof, and ingredients thereof.

In some embodiments, the instructions for tracking comprise instructions for obtaining a container equipment record for each container in the plurality of containers from the database. In some embodiments, each such container equipment record is created at a time prior to execution of the instructions for tracking. In some embodiments, the instructions for specifying a blend comprise instructions for obtaining a unit operation record from the database that specifies the first quantity, the first container, the second quantity, and the second container. In some embodiments, the at least first container is in a first plant and said at least second container is in a second plant.

In some embodiments, the module further comprises instructions for generating, on a periodic basis, a report comprising any combination of, for example, (i) amounts of distilled spirits in the plurality of containers at a beginning of a period; (ii) amounts received; (iii) amounts dumped as alcohol flavor; (iv) amounts mixed with wine; (v) amounts dumped for further processing; (vi) gains; (vii) amounts bottled or packaged; (viii) amounts withdrawn without payment of tax; (ix) amounts withdrawn for research, development, or testing; (x) amounts destroyed; (xi) amounts used for redistillation; (xii) amounts lost; and (xiii) amounts on hand at the end of the end of said period. Advantageously, in some embodiments, the amounts are in quantities of proof gallons. In some embodiments, amounts are reported separately for bulk ingredients and finished product. In some embodiments, amounts are reported separately for each plant number or plant location that houses a container in the plurality of containers. In some embodiments, period is a day, week, month, or year. In some embodiments, the report includes quantities of bulk spirits that have been dumped into processing, imported, bottled, bottled in bond, bottled for export during the period. In some embodiments, the quantities are itemized by: (i) alcohol and neutral spirits other than vodka; (ii) blended straight whiskey; (iii) blended whiskey with neutral spirits; (iv) blended whisky with light whiskey; (v) blended light whiskey; (vi) all other blends of 100% whiskey; (vii) imported scotch; (viii) imported Canadian whiskey; (ix) domestic whiskey distilled at 160 proof and under; (x) domestic whiskey distilled at over 160 proof; (xi) brandy distilled at 170 proof and under; (xii) brandy distilled at over 170 proof; (xiii) Puerto Rican rum; (xiv) Virgin Islands rum; (xv) domestic rum; (xvi) gin; (xvii) vodka; (xviii) cordial, liquors and specialties; and (xiv) tequila.

4. BRIEF DESCRIPTION OF THE DRAWINGS

Like reference numerals refer to corresponding parts throughout the several views of the drawings.

5. DETAILED DESCRIPTION

The present invention provides systems and methods for supporting global, multi-site corporations in addition to single sites. The present invention provides systems and methods for supporting parallel product operations as well as single product operations. Product traceability both in the forward and reverse direction is supported. Such traceability improves upon prior art compliance data collection and allows for automated reporting to regulatory agencies and management. Advantageously, operational information is made available in real time due to the support for real time work order entries. The systems and methods of the present invention provide visibility into enterprise processing resources so that it is possible to see, at all times, what is being processed for various production lines. Furthermore, real time views into storage/inventory are supported. The systems and methods of the present invention further support standard operating procedures for multisite production. The systems and methods further provide electronic planning and execution so that users can automatically make updates to inventory and distilled spirit blend characteristics and compositions.

In some embodiments, computers, computer program products, systems, and methods for gauging distilled spirits during production of such spirits are provided. The distilled spirits may be any liquid containing ethanol and water in specified proportions. Fermentation liquids, distillates or mixtures thereof or of synthetic ethanol and water may all be gauged. Nonlimiting examples of the base for the fermentation of such distilled spirits include, but are not limited to, grains such as corn, wheat, barley, rye or the like, roots or tubers such as potato or beet or the like, fruits such as grape, apple, cherry, orange or the like or other plant part such as sugar cane, cactus or the like. The particular ethanol containing liquids used will dictate which of the commonly recognized categories of distilled spirits, such as rum, scotch, whisky, brandy, bourbon whisky, eau de vie, tequila, vodka, liquors, and the like that are made. The ethanol content in the distilled spirits may vary from 2% to 100%, though it is preferable to maintain the ethanol content of the liquid from about 45% to about 85% in some embodiments.

Figure 1:
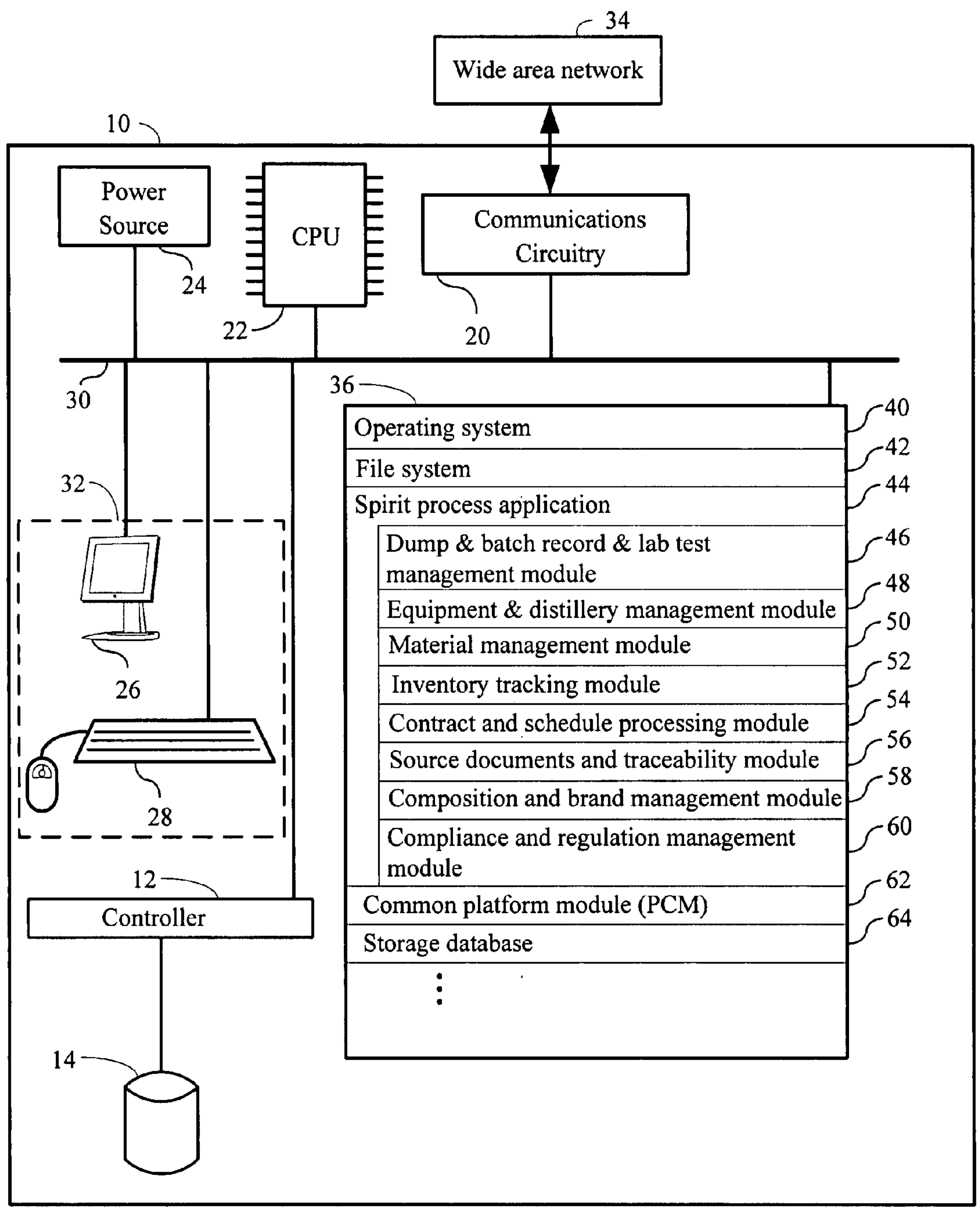
FIG. 1 illustrates a computer system for tracking the composition and age of spirits, spirituous liquor and distilled spirits during production in accordance with an embodiment of the present invention.

FIG. 1 details an exemplary system that supports the functionality described above. The system can, for example, be used to support and track multi-site business models, multibrand, multi production systems, and different processes within plants. Further, the system can support corporate views such as organization/site, products, brands, transfers, facilities, inventories, activities and movements, approved equipment, material, standards, process recipes, and approved formulae. The system can further support versioning and approval of important data, such as process recipes/unit operations, equipment, material, standards, products, brands, and batch record templates. In some embodiments, the system provides the following: an enterprise user interface, a material library, an equipment library, a standards library, a process/recipe library, brand management, processing (batch record planning), quality management, and enterprise blend traceability.

The system is preferably a computer system 10 having:

- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 as well as other input and output devices (e.g., a mouse);
- a network interface card 20 for connecting to any wired or wireless communication network 34 (e.g., a wide area network such as the Internet);
- an internal bus 30 for interconnecting the aforementioned elements of the system; and
- a power source 24 to power the aforementioned elements.

Operation of computer 10 is controlled primarily by operating system 40, which is executed by central processing unit 22. Operating system 40 can be stored in system memory 36. In a typical implementation, system memory 36 includes:

- file system 42 for controlling access to the various files and data structures used by the present invention;
- a spirit process application 44 for tracking the composition and age of distilled spirits during production;
- a common platform module (PCM) 62 for handling lower level computer services for spirit process application 44 and other applications; and
- a storage database 64 for storing persistent data generated by or tracked by spirit process application 44.

In more detail, PCM 62 provides a configurable meta model, and allows users to define workflow processes, alerts, and integrations. PCM 62 provides an automatic audit trail across all important data such as approval history, and change history. PCM 62 enables web-based and "point and click" interface that can be access in the distillery, at home, or while traveling. PCM 62 further provides for the ability to search across the enterprise for available and approved equipment, material, and process recipes.

As illustrated in FIG. 1, computer 10 comprises storage database 64. Database 44 can be any form of data storage system including, but not limited to, a flat file, a relational database (SQL), and an on-line analytical processing (OLAP) database (MDX and/or variants thereof). In some specific embodiments, database 44 is a hierarchical OLAP cube. In some specific embodiments, database 44 comprises a star schema that is not stored as a cube but has dimension tables that define hierarchy. Still further, in some embodiments, database 44 has hierarchy that is not explicitly broken out in the underlying database or database schema (e.g., dimension tables are not hierarchically arranged). In some embodiments, database 44 is a single database that includes records of the composition and age of distilled spirits during production and storage. In other embodiments, database 44 in fact comprises a plurality of databases that may or may not all be hosted by the same computer 10. In such embodiments, some component databases of database 44 are stored on computer systems that are not illustrated by FIG. 1 but that are addressable by wide area network 34.

It will be appreciated that many of the modules illustrated in FIG. 1 can be located in one or more remote computers. Such remote computers may in another room, another building, another location, another city, town, or state, or country. For example, some embodiments of the present application are web service-type implementations. In such embodiments, spirit process application 44 and other modules used by distilled spirit workers can reside on a client computer (e.g., a handheld device such as a blackberry, Trio, personal digital assistant, lap top computer, desktop computer, or the like) that is in wired or wireless communication with computer 10 via network 34. In some embodiments, for example, spirit process application 44 can be an interactive web page.

In some embodiments, database 44 and the program modules of the present invention (e.g. modules 42, 62, and 64) illustrated in FIG. 1 are on a single computer (computer 10) and in other embodiments the database 44 and modules are hosted by several computers (not shown). Any arrangement of database 44 and the modules illustrated in FIG. 1 on one or more computers is within the scope of the present invention so long as these components are addressable with respect to each other across network 34 or other electronic means (e.g., wireless means). Thus, the present invention fully encompasses a broad array of computer systems.

The present invention can be implemented as a computer program product that comprises a computer program mechanism embedded in a computer readable storage medium. For instance, the computer program product could contain the program modules shown in FIG. 1. These program modules may be stored on a CD-ROM, DVD, magnetic disk storage product, or any other computer readable data or program storage product. The software modules in the computer program product can also be distributed electronically, via the Internet or otherwise, by transmission of a computer data signal (in which the software modules are embedded) on a carrier wave. Any of the methods of the present invention can be implemented in one or more computers. Further still, any of the methods of the present invention can be implemented in one or more computer program products.

One aspect of the present invention comprises computer systems that can carry out any of the methods, or parts thereof, disclosed in this application. Another aspect of the present invention comprises computer program products that can carry out any of the methods, or parts thereof, disclosed in this application.

Figure 2:
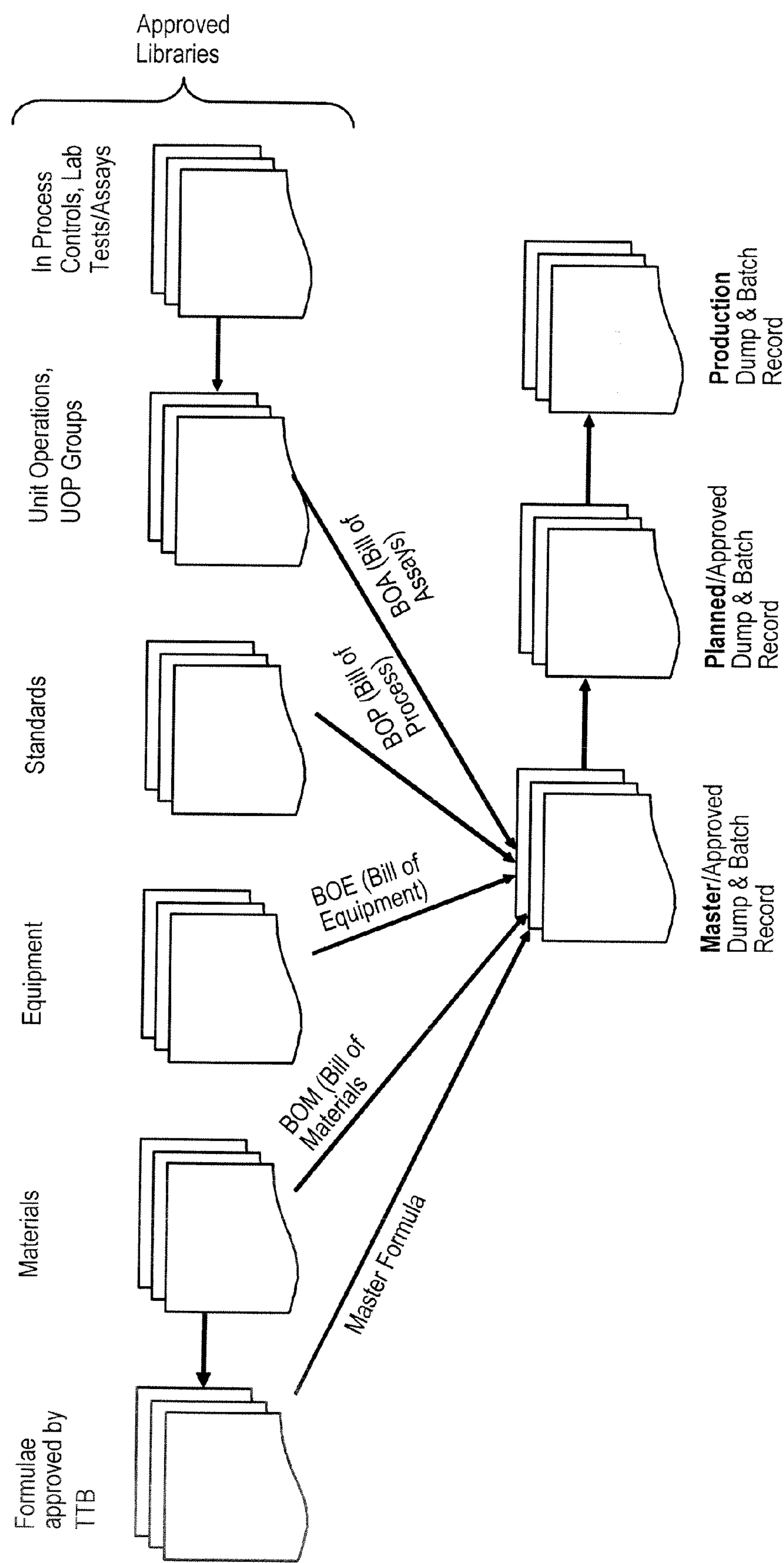
FIG. 2 illustrates the overall process flow supported by a spirit process application in accordance with an embodiment of the present invention.

Referring to FIG. 1, more details of spirit process application 44 in accordance with an embodiment of the present invention will now be disclosed. The overall process flow supported by spirit process application 44 is illustrated in FIG. 2. Spirit process application 44 allows a user to store a detailed description of each piece of equipment that will be used in distilled spirit production, as well as to define the processes that will be used to make the distilled spirits in terms of starting materials, fermentation periods, blends, and other events. Compositions and ages of liquids stored in each piece of equipment (e.g., fermentation tanks) are continuously tracked in a variety of ways. For instance, when a blend occurs, the systems and methods of the present invention can compute the composition of the blend based on the composition of the distilled spirits that were used to make the blend. Further, the present invention allows production workers to enter detailed measurements made of the starting ingredients, intermediate products, and final products of the production process. Such measurements can by input any number of ways (e.g., through PDAs, interactive web pages, desktop computers in wired or wireless communication with system 10). In some embodiments, estimates of loss due to evaporation are computed as a function of equipment type and temperature. In some advantageous embodiments, correction for true volume as a function of proof and temperature is automatically computed. Because of the aforementioned features, application 44 is able to more accurately predict the final composition of a distilled spirit and to reconcile quantities of ethanol produced versus quantities of ethanol distributed. The following modules are exemplary. Furthermore, it will be appreciated that features that are described in one module below, can in fact, be in a different module described below.

Dump and batch record and lab test management module 46. Dump and batch record and lab test management module 46 supports execution of operations on batch records to move spirits within a distillery. Module 46 allows a user to edit modify, create and/or otherwise specify dump and batch record template details, dump and batch record template names, project names, product identifiers, product year comments, target year, brand name, brand identifier, product description, requested material name, requested delivery date, quantity, operating mode (e.g., supply), status (e.g., pending approval, approved), product name, target quantity (e.g., in kilograms), regulatory designation, recipe identifier, manufacturing site, site identifier, description, expected yield, target start date, target end date, planned number of lots, comments, bill of material name, and bill or material identifier. Additionally, a variety of actions can be performed by module 46, including importing an available master bill of material, locating a master bill of material, adding material, adding material using variables, and/or validating a bill of material. With module 46, multi-site, integrated planning and execution is possible using all the libraries in the system (equipment, material, standards, controls, etc). Approved batch records may be reissued to save time in process/data entry errors and time delays. Module 46 further provides integration with batch record planning to provide unified activity and analysis information and sample management for containers.

Using module 46, one can perform any combination of the following activities: remove a dump and batch record, add a dump and batch record, manage a dump and batch record, reserve a bill of equipment, manage allocation, validate dump and batch record templates, save a scaled bill of material as a master bill of material, activate or deactivate a dump and batch record, take action, set permissions, or purge revisions. Using module 46, a user can define a new allocation request. The new allocation request is based on the bill of material for the process step. Identifying information is specified for the allocation request such as project identifier, campaign identifier, work order template, the user identifier of the requester, the user identifier of the responsible person, operating mode (e.g., development), and comments.

The systems and methods of the present invention support a number of distilled spirit specific activities that involve malting (floor & steeps), milling (machines), mashing (mash tubs), fermenting (washback), distilling (wash stills), and maturation (barrels, casks). Examples of malting activities include screening grains (barley, etc.) for impurities, soaking in water (steeps), draining, germinating (with frequent turning), and drying. Examples of milling activities include cleaning and crushing, grinding and transferring to mash tubes. Examples of mashing include mixing grist with hot water, stirring, draining and transfer to washback. An example of fermenting (washback) is the addition of yeast. Examples of distilling activities includes taking wash from the fermenting process into a still and heating and receiving the spirit from the vessel as well as transferring spirit back to a still for slow distilling. Examples of maturation include transferring a spirit to barrels or casks and aging for a number of years. Advantageously, the present invention provides template constructs for each of these distilled spirit specific processing activities. These constructs can be combined into processes that can then be used to process distilled spirits. Each such construct provides suitable parameters for the activity such as quantities, conditions, controls and alerts.

Equipment and distillery management module 48. Equipment and distillery management module 48 allows for the modeling of different hierarchies and types of equipment with detailed characteristics, equipment qualification, and the reservation of equipment while authoring batch records. Module 48 allows a user to create, modify, and store a bill of equipment. Furthermore, a user can use module 48 to perform actions such as duplicate equipment, remove equipment, manage a reservation for equipment, manage equipment activity (e.g., cleaning, storage), manage equipment qualification, specify an equipment loan, specify an equipment lease, manage equipment, change the site of equipment, activate equipment, deactivate equipment, take action, and set permissions.

In some embodiments, module 48 is used to manage records of each piece of equipment at a single distilled spirit production site. In some embodiments, module 48 is used to manage records of each piece of equipment at multiples production sites. Such records specify equipment category (e.g., tank, barrel, mill, pot still, cast, storage silo, high column plate still, mash tub, quashback, etc.). More detailed information is also stored in such records. For example, in the case where the equipment is a tank, the record may have fields such as equipment/tank, equipment identifier, equipment category, equipment name, equipment type (e.g., fixed), equipment condition, location, vendor, tank capacity volume, tank capacity weight, tank status, equipment status (e.g., draft), equipment site (e.g., global), equipment operating mode (e.g. development, production, etc.), equipment effective start and end date, tank storage location, required cleaning limit, to name a few possible fields.

Material management module 50. Material management module 50 facilitates tracking of material requests, receipt of materials, as well as dispensement for each product, brand, and batch record. Module 50 enables one click traceability for all blends, tanks, activity, raw materials including additives to bottling Using module 50, a user can originate, copy or modify a bill of material that specifies one or more ingredients for use in the production of distilled spirits. The types of materials that can be managed by module 50 includes, but is not limited to, chemicals, blends, filters, additives, and raw materials (e.g., grains, grapes, fruits, etc.). Further, module 50 can be used to manage the attributes of such materials. Material attributes include, but are not limited to, material type, material description, item code, material name, item identifier, common name, special handling, safety storage condition, environmental storage requirements, security storage condition, sampling exemption flag, low inventory amount warning, solvate form, material physical properties (e.g., viscosity, boiling point, partial pressure, purity, etc.). Module 50 can further be used to define the effective start date of a given material (e.g., when it first became available for use), effective end date (e.g., when the material should no longer be used in a process), correct workflow (e.g., which processes the material is currently supporting), business object status, created time, modified time, created user (e.g., who entered a description of the material into module 50), and modified user (e.g., who last modified an attribute of the material in module 50). Moreover, module 50 can handle material allocation and dispense requests, material inventory tracking, material orders, receipt of material, and master bill of materials.

Inventory tracking module 52. Inventory tracking module 52 provides blend inventory across all sites to determine processing. Thus, at all times, the quantities of blends in storage and in processing are traced.

Contract and schedule processing module 54. Contract and schedule processing module 54 tracks customer orders and schedules tracking. Module 54 supports unit operations (e.g., the mixing of two starting ingredients, etc.). A unit operation specifies any combination of the following: the observation required, comments, the site where the unit operation takes place, a notification group to be notified when the unit operation takes places, a description of the unit operation, a functional purpose of the unit operation, a unit operation type (e.g., addition), a unit operation name (e.g. add sugar), a unit operation identifier, a current workflow where the unit operation is presently used, an effective start date and end date for use of the unit operation, an indication of when the unit operation was modified, an indication of who created the unit operation, and an indication of who modified the unit operation. Module 54 further supports unit actions. A unit action data structure can include a unit action description, whether or not second person verification of the unit action is required (yes/no), and instructions (e.g. desired weight of syrup 1.35, record tare weight, actual weight). Control variables may be inserted into unit actions. A control variable may have any combination of: a control name (e.g., temperature), a control description (e.g., measure temperature in tank), a data type (e.g., float, integer), an assay indicator (yes/no), a before action threshold (e.g. a minimum threshold, a maximum threshold, a target value, and a unit of measurement such as degrees Celsius), a before threshold precision, an after action threshold (e.g. a minimum threshold, a maximum threshold, a target value, and a unit of measurement such as degrees Celsius), an after action precision, an alert type, an alert threshold (e.g., minimum, maximum, target, unit of measurement such as wine gallons), an alert threshold, a precision notebook reference and a comment.

Source documents and traceability module 56. Source documents and traceability module 56 provides an interface for forward and reverse tracing from grain to the final bottled distilled spirits. Such tracing includes, but is not limited to, (i) finding all lots made under a product/brand, (ii) tracing a lot to a template and approved formula, (iii) tracing a lot back to intermediate blends and all source ingredients, (iv) tracing from a source component through all blends to a bottle, bulk, product, or brand, etc., and (v) tracking proof and age for label compliance.

Composition and brand management module 58. Composition and brand management module 58 allows for product, brand and blend traceability to be maintained. Module 58 permits the tracking of the composition and age of distilled spirits throughout production. Module 58 is facilitated by the use of composition records that describe material characteristics. Representative characteristics include, but are not limited to, any combination of age in years or months, color, intensity (e.g., medium), quantity in proof gallons, true proof, obscuration, invoice proof gallons, proof gallons received, loss/gain in proof gallons, quantity in wine gallons, apparent proof, tax owed, effective start date and effective end date. Advantageously, in some embodiments, module 58 provides correction for true volume as a function of proof and temperature.

Compliance and regulation management module 60. Advantageously, compliance and regulation management module 60 automatically populates TTB forms, including forms 5110.11, 5110.28, 5110.40, and their equivalents. For example, TTB form 5110.28 requires a distiller to report to the government, on a monthly basis, in quantities of proof gallons, amounts of distilled spirits on hand at the first of month, amounts received, amount dumped as alcohol flavor, amounts mixed with wine, amounts dumped for further processing, gains, amounts bottled or packaged, amounts withdrawn without payment of tax for addition to wine (or for use in hospitals, for scientific use, or for educational use), amount withdrawn for research, development, or testing (including government samples), amounts destroyed, amounts used for redistillation, amounts lost, and amounts at hand at the end of the month. Such amounts are reported separately for bulk ingredients and finished product. Such forms are broken down by plant number and plant location.

Furthermore, the TTB requires, through usage of TTB form 5110.28 part IV, that the processing of the distilled spirits for nonindustrial purposes be reported on a monthly basis. Such reporting includes quantities of bulk spirits that have been dumped into processing (in whole proof gallons), quantities that have been imported (in whole proof gallons), quantities that have been bottled (in whole wine gallons), quantities that have been bottled in bond (e.g., pursuant to title 27 of the Code of Federal Regulations, Section 5.42(b)), and quantities that have been bottled for export (in whole wine gallons). Such quantities are itemized on the forms, for example, by (i) alcohol and neutral spirits other than Vodka, blended straight whiskey, blended whiskey with neutral spirits, blended whisky with light whiskey, blended light whiskey, all other blends of 100% whiskey, imported scotch, imported Canadian whiskey, all other imported whiskeys, domestic whiskey distilled at 160 proof and under, domestic whiskey distilled at over 160 proof, brandy distilled at 170 proof and under, brandy distilled at over 170 proof, Puerto Rican rum, Virgin Islands rum, domestic rum, other imported rum, gin, vodka, cordial & liquors & specialties, cocktails & drinks, and tequila.

Furthermore, the TTB requires, through use of form TTB5110.11, a monthly report on storage operations. For instance, storage of quantities of distilled spirits in the form of (i) whiskey that is distilled at less than 160 proof and under, (ii) whiskey that is distilled at over 160 proof, (iii) brandy that is distilled at less than 170 proof, (iv) brandy that is distilled at over 170 proof, (v) rum, (vi) gin, (vii) vodka, (viii) alcohol and spirits that are 190 proof and over, and (ix) alcohol and spirits that are 190 proof and lower must each be reported separately in order to comply with TTB regulations. Furthermore, for each such category, many different transactions must be reported such as (i) amounts on hand at the first of the month, (ii) amount deposited in bulk storage, (iii) amount received from customs custody, (iv) amount returned to bulk storage, (v) tax paid, amount of tax not paid because of (a) use of the United States, (b) hospital, scientific, and educational use, (c) export, (d) transfer to a foreign-trade zone, (e) use as supplies on vessels and aircraft, (f) transfer to a bonded winder, (g) transfer to CBW, or (h) research development and testing, (vi) amounts transferred to a processing account, (vii) amounts transferred to a production account, (viii) amounts transferred to other bonded premises, (ix) amounts destroyed, (x) other losses, and (xi) amounts on hand at the end of the month.

The TTB also requires, through use of form TTB5110.40, a monthly report on production operations. For instance, transactional information for distilled spirits in the form of (i) whiskey that is distilled at less than 160 proof and under, (ii) whiskey that is distilled at over 160 proof, (iii) brandy that is distilled at less than 170 proof, (iv) brandy that is distilled at over 170 proof, (v) rum, (vi) gin, (vii) vodka, (viii) alcohol and spirits that are 190 proof and over, and (ix) alcohol and spirits that are 190 proof and lower must each be reported separately in proof gallons in order to comply with TTB regulations. Furthermore, for each such category, many different transactions are reported such as (i) tax payment, (ii) use of the United States, (iii) hospital, scientific, or educational use, (iv) export, (v) transfer to foreign trade zone, (vi) transfer to CMBW, (vii) use as supplies on vessels or aircraft, (viii) use in wine production, (ix) amounts entered into a processing account, (x) amounts entered into a storage account, (xi) amounts withdrawn for research development or testing, (xii) total amounts produced, (xiii) total amounts received for redistillation. Furthermore, the production of distilled spirits of 190 proof or greater must be reported by kind of material used (e.g., grain, fruit, molasses, ethyl sulfate, ethylene gas, sulphite liquors, from redistillation, each in proof gallons. The production of whisky by kind (bourbon, corn, rye, light) and cooperage (proof gallons new cooperage, proof gallons used cooperage, proof gallons deposited in tanks) must be reported on a monthly basis. Furthermore, production of branding by kind (grape brandy, all other brandy, neutral grape brandy, all other neutral brandy) must be reported in proof gallons. Amounts of distilled spirits used in redistillation must be reported by kind of spirits in units of proof gallons. Further still, materials used in production of distilled spirits, and used in manufacture of substance other than distilled spirits, in processes yielding distilled spirits as a by-product are separately reported in pounds and/or gallons. Materials such as grain and grain product (e.g., corn, rye, malt, wheat, sorghum grain, barley, etc.), fruit and fruit product (e.g., grape), cane and cane product (e.g., molasses) and other materials (e.g., ethyl sulfate, ethylene sulfate, sulphite liquors, butane gases, etc.) are separately reported.

6. EXAMPLES

The following examples are intended to highlight issues that arise in the production of distilled spirits and how the present invention advantageously addresses such issues.

Propagate composition. Consider the case where there is a first group of 100 barrels with producer 1 that each have a first lot number, a second group of 100 barrels with producer 2 that each have a second lot number, and a third group of 100 barrels with producer 3 that each have a third lot number. A third of each of the three groups is blended together in a tank. The exact age of the resultant blend is needed. In accordance with the present invention, the age of the blend is automatically recorded as the age of the youngest group of distilled spirits in the blend.

Execution. The present invention tracks movements, volume losses and gains for TTB reports. For example, if there are 100 barrels, and 5000 gallons of brandy is placed into those barrels, the average fill is 50 gallons per barrel. In another example, if you dump 30 barrels, you may get 1200 gallons instead of 1500 gallons due to evaporation, leaks etc. The present invention tracks such movements and events for the TTB reports.

Marking equipment. In accordance with TTB regulations, all equipment must be marked either as for storage of distilled spirits or for processing of distilled spirits. Advantageously, the equipment records of the present invention have a field for equipment records which specifies whether the equipment is for storage or for processing. In some embodiments, anything in barrel is “storage” and is reported on storage operations.

Other examples. One aspect of the invention provides a method of propagating distilled spirit compositions throughout a production process. In this method, the composition of distilled spirits in each of a plurality of containers used in the production of a distilled spirit product is tracked. For instance, the composition and age of distilled spirits is recorded in a database as a set of material records, where each material record includes information about the composition of distilled spirits in a container in the plurality of containers. In some embodiments, the plurality of containers comprises three or more containers, five or more containers, ten or more containers, or one hundred or more containers. Each material record may reference an equipment record that provides more details of the specific container or containers associated with a given material record. In the method a first quantity of a first distilled spirit from at least a first container (e.g. a single container, two or more containers, three or more containers, more than five containers) in the plurality of containers is blended with a second quantity of a second distilled spirit from at least a second container (e.g. a single container, two or more containers, three or more containers, more than five containers) in the plurality of containers to form a third quantity of a third distilled spirit. The third quantity of the third distilled spirit is placed into at least a third container in the plurality of containers. In some embodiments, the first and second quantities are blended together by placing them directly into the third container. Advantageously, the composition of the distilled spirits in the third container is automatically computed based on the known composition of the first quantity of the first distilled spirit, the known composition of the second quantity of the second distilled spirit, and the known composition and quantity of distilled spirits in the third container at a time prior to when the first and second quantities were placed in the third container. The composition, quantity and age of distilled spirits in the first container, the second container, and the third container is then stored. In some embodiments, the aforementioned storing step comprises storing the composition, quantity, and age of distilled spirits in the first container, the second container, and the third container in a database.

Advantageously, in some embodiments, not only can compositions of distilled spirits be propagated throughout a production process, they can also be subjected to verification. For instance, hydrometer readings and temperature reading of the first tank, the second tank, and/or the third tank can be made and recorded. Such readings serve to verify calculated compositions based on composition propagation. For instance, in some embodiments, such readings are used to compute a true percent proof of the composition in the first tank, the second tank, or the third tank based using lookup table that provides true percent proof as a function of hydrometer reading and temperature. In some embodiments, these true percent proof calculations are stored in a database. As another example, in some embodiments, the inventive methods of the present example further comprise (i) receiving a measured volume of the first tank, the second tank, or the third tank, (ii) computing a correction of the measured volume, and (iii) updating a composition of the first tank, the second tank, or the third tank based on the correction of the measured volume. Such updates to the measured volume (e.g. the correction of the measure volume) may be stored in a database. In some embodiments, tracking of the composition of distilled spirits in a plurality of containers is facilitated by obtaining a container equipment record for each container in the plurality of containers from a database. Exemplary equipment records store, for example, equipment category (e.g., tank, barrel, mill, pot still, cast, storage silo, high column plate still, mash tub, quashback, etc.), equipment identifier, equipment category, equipment name, equipment type (e.g., fixed), equipment condition, location, vendor, capacity volume, capacity weight, status, equipment status (e.g., draft), equipment site (e.g., global), equipment operating mode (e.g. development, production, etc.), equipment effective start and end date, storage location, required cleaning limit, to name a few possible fields. In some embodiments, each such container equipment record is created at a time prior to tracking distilled spirits throughout a product process. In some embodiments, a container in the plurality of containers is a tank, barrel, mill, pot still, cast, storage silo, high column plate still, mash tub, or quashback.

In some embodiments, the blending described earlier in this example comprises obtaining a unit operation record that specifies the first quantity, the first container, the second quantity, and the second container. This unit operation record may, for example, be stored in a database. The methods described in this example may be implemented in a software program that operates on an enterprise level in which there are multiple plants. So, the at least first container can easily be in a first plant and the at least second container can easily be in a second plant. Because composition amounts for each of the plurality of containers are tracked, tax forms can be automatically populated. For example, on a periodic basis, a report comprising any combination of information can be generated: (i) amounts of distilled spirits in the plurality of containers at a beginning of a period; (ii) amounts received; (iii) amounts dumped as alcohol flavor; (iv) amounts mixed with wine; (v) amounts dumped for further processing; (vi) gains; (vii) amounts bottled or packaged; (viii) amounts withdrawn without payment of tax; (ix) amounts withdrawn for research, development, or testing; (x) amounts destroyed; (xi) amounts used for redistillation; (xii) amounts lost; and (xiii) amounts on hand at the end of the end of the period. Advantageously, such amounts can be tracked in quantities of proof gallons. In some embodiments, the amounts are reported separately for bulk ingredients and finished product. In some embodiments amounts are reported separately for each plant number or plant location that houses a container in the plurality of containers. The periodic basis can be, for example, a day, a week, a month, a year, or any other period specified by a governmental reporting agency such as the United States trade bureau. In some embodiments, the report includes quantities of bulk spirits that have been dumped into processing, imported, bottled, bottled in bond, or bottled for export during the period. In some embodiments, the quantities are itemized by (i) alcohol and neutral spirits other than vodka; (ii) blended straight whiskey; (iii) blended whiskey with neutral spirits; (iv) blended whisky with light whiskey; (v) blended light whiskey; (vi) all other blends of 100% whiskey; (vii) imported scotch; (viii) imported Canadian whiskey; (ix) domestic whiskey distilled at 160 proof and under; (x) domestic whiskey distilled at over 160 proof; (xi) brandy distilled at 170 proof and under; (xii) brandy distilled at over 170 proof; (xiii) Puerto Rican rum; (xiv) Virgin Islands rum; (xv) domestic rum; (xvi) gin; (xvii) vodka; (xviii) cordial, liquors and specialties; and tequila.

7. REFERENCES CITED; MODIFICATIONS

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A computer program product, tangibly embodied in a computer-readable memory, including instructions operable to cause data processing apparatus to:

track the composition of distilled spirits in each of a plurality of containers used in the production of a distilled spirit product;

specify a blend of a first quantity of a first distilled spirit from at least a first container in the plurality of containers with a second quantity of a second distilled spirit from at least a second container in the plurality of containers to form a third quantity of a third distilled spirit;

specify the placement of the third quantity of the third distilled spirit into at least a third container in the plurality of containers;

compute the final composition of the distilled spirits in the third container based on the known composition of the first quantity of the first distilled spirit, the known composition of the second quantity of the second distilled spirit, and the known composition in the third container at a time prior to the placement of the third quantity of the third distilled spirit into the third container;

store information about the final composition, quantity and age of the distilled spirits in the first container, the second container, and the third container;

use the stored information about the final composition, quantity and age of the distilled spirits to compute an amount of taxes owed on the distilled spirits in the first container, the second container, and the third container; and perform compliance tasks with respect to the distilled spirits including automatically populating a plurality of forms for automatic periodic submission to a regulatory agency.

2. The computer program product of claim 1, further comprising instructions operable to cause the data processing apparatus to:

receive a hydrometer reading and a temperature reading of the first container, the second container, or the third container;

compute a true percent proof of the composition in the first container, the second container, or the third container based on the hydrometer reading and the temperature reading; and update the composition of the first container, the second container, or the third container based on the true percent proof.

3. The computer program product of claim 2, further comprising instructions operable to cause the data processing apparatus to store the updated composition of the first container, the second container, or the third container in a database.

4. The computer program product of claim 1, further comprising instructions operable to cause the data processing apparatus to:

receive a measured volume of the first container, the second container, or the third container;

compute a correction of the measured volume; and update a composition of the first container, the second container, or the third container based on the correction of the measured volume.

5. The computer program product of claim 4, further comprising instructions operable to cause the data processing apparatus to store the correction of the measured volume in a database.

6. The computer program product of claim 4, further comprising instructions operable to cause the data processing apparatus to access a lookup table stored in a memory, the lookup table facilitating the correction of volume as a function of true percent proof and temperature.

7. The computer program product of claim 1, wherein the distilled spirits in the third container is whiskey, blended whiskey with neutral spirits, blended whisky with light whiskey, blended light whiskey, imported scotch, imported Canadian whiskey, domestic whiskey distilled at 160 proof and under, domestic whiskey distilled at over 160 proof, brandy distilled at 170 proof and under, brandy distilled at over 170 proof, Puerto Rican rum, Virgin Islands rum, domestic rum, gin, vodka, a cordial, a liquor, or tequila.

8. The computer program product of claim 1, wherein the instructions for tracking comprise instructions for obtaining a container equipment record from a database for each container in the plurality of containers.

9. The computer program product of claim 8, wherein each the container equipment record is created before the instructions for tracking that container equipment record are executed.

10. The computer program product of claim 1, wherein the third container is a tank, barrel, mill, pot still, cast, storage silo, high column plate still, mash tub, or quashback.

11. The computer program product of claim 1, wherein the instructions for specifying a blend comprise instructions for obtaining a unit operation record from a database, the unit operation record specifying the first quantity, the first container, the second quantity, and the second container.

12. The computer program product of claim 1, wherein the at least a first container is in a first plant and the at least a second container is in a second plant.

13. The computer program product of claim 1, further comprising instructions operable to cause a data processing apparatus to display or output the composition and quantity of distilled spirits in the first container, the second container, and the third container, wherein outputting includes outputting to a user interface device, a monitor, a computer-readable storage medium, a computer-readable memory, or a local or remote computer system.

14. An apparatus, comprising:

a central processing unit; and a memory coupled to the central processing unit, the memory storing a module for propagating distilled spirit compositions throughout a production process, the module comprising instructions operable to cause the central processing unit perform one or more operations, the module comprising:

instructions to track the composition of distilled spirits in each of a plurality of containers used in the production of a distilled spirit product;

instructions to specify a blend of a first quantity of a first distilled spirit from at least a first container in the plurality of containers with a second quantity of a second distilled spirit from at least a second container in the plurality of containers to form a third quantity of a third distilled spirit;

instructions to specify the placement of the third quantity of the third distilled spirit into at least a third container in the plurality of containers;

instructions to compute the final composition of the distilled spirits in the third container based on the known composition of the first quantity of the first distilled spirit, the known composition of the second quantity of the second distilled spirit, and the known composition in the third container at a time prior to the placement of the third quantity of the third distilled spirit into the third container;

instructions to store information about the final composition, quantity and age of the distilled spirits in the first container, the second container, and the third container;

instructions to use the stored information about the final composition, quantity and age of the distilled spirits to compute an amount of taxes owed on the distilled spirits in the first container, the second container, and the third container; and instructions to perform compliance tasks with respect to the distilled spirits including automatically populating a plurality of forms for automatic periodic submission to a regulatory agency.

15. The apparatus of claim 14 wherein the memory stores a database and wherein the storing step comprises storing the final composition, quantity and age of distilled spirits in the first container, the second container, and the third container in the database.

16. The apparatus product of claim 14, further comprising instructions operable to cause the data processing apparatus to periodically generate a report comprising any combination of:

(i) amounts of distilled spirits in the plurality of containers at a beginning of a period;

(ii) amounts received;

(iii) amounts dumped as alcohol flavor;

(iv) amounts mixed with wine;

(v) amounts dumped for further processing;

(vi) gains;

(vii) amounts bottled or packaged;

(viii) amounts withdrawn without payment of tax;

(ix) amounts withdrawn for research, development, or testing;

(x) amounts destroyed;

(xi) amounts used for redistillation;

(xii) amounts lost; and (xiii) amounts on hand at the end of the end of said period.

17. The apparatus of claim 16, wherein amounts are in quantities of proof gallons.

18. The apparatus of claim 16, wherein amounts are reported separately for bulk ingredients and finished product.

19. The apparatus of claim 16, wherein amounts are reported separately for each plant number or plant location that houses a container in the plurality of containers.

20. The apparatus of claim 16, wherein the period is a day, week, month, or year.

21. The apparatus of claim 16, wherein the report includes quantities of bulk spirits that have been dumped into processing, imported, bottled, bottled in bond, bottled for export during the period.

22. The apparatus of claim 21, wherein the quantities are itemized by:

(i) alcohol and neutral spirits other than vodka;

(ii) blended straight whiskey;

(iii) blended whiskey with neutral spirits;

(iv) blended whisky with light whiskey;

(v) blended light whiskey;

(vi) all other blends of 100% whiskey;

(vii) imported scotch;

(viii) imported Canadian whiskey;

(ix) domestic whiskey distilled at 160 proof and under;

(x) domestic whiskey distilled at over 160 proof;

(xi) brandy distilled at 170 proof and under;

(xii) brandy distilled at over 170 proof;

(xiii) Puerto Rican rum;

(xiv) Virgin Islands rum;

(xv) domestic rum;

(xvi) gin;

(xvii) vodka;

(xviii) cordial, liquors and specialties; and (xiv) tequila.

23. The apparatus of claim 22 wherein the at least a third container is the at least a first container or the at least a second container.

24. The apparatus of claim 14, wherein the module further comprises instructions operable to cause the central processing unit to display or output the composition and quantity of distilled spirits in the first container, the second container, and the third container, and wherein outputting includes outputting to a user interface device, a monitor, a computer-readable storage medium, a computer-readable memory, or a local or remote computer system.

25. A method of propagating distilled spirit compositions throughout a production process, the method comprising:

tracking the composition of distilled spirits in each of a plurality of containers used in the production of a distilled spirit product;

blending a first quantity of a first distilled spirit from at least a first container in the plurality of containers with a second quantity of a second distilled spirit from at least a second container in the plurality of containers to form a third quantity of a third distilled spirit;

placing the third quantity of the third distilled spirit into at least a third container in the plurality of containers;

computing the composition of the distilled spirits in the third container based on the known composition of the first quantity of the first distilled spirit, the known composition of the second quantity of the second distilled spirit, and the known composition in the third container at a time prior to the placement of the third quantity of the third distilled spirit into the third container;

storing information about the final composition, quantity and age of distilled spirits in the first container, the second container, and the third container;

using the stored information about the final composition, quantity, and age of distilled spirits to compute an amount of taxes owed on the distilled spirits in the first container, the second container, and the third container; and performing compliance tasks with respect to the distilled spirits including automatically populating a plurality of forms for automatic periodic submission to a regulatory agency.

26. The method of claim 25 wherein the storing step comprises storing the final composition, quantity, and age of distilled spirits in the first container, the second container, and the third container in a database.

27. The method of claim 25, the method further comprising: receiving a hydrometer reading and a temperature reading of the first container, the second container, or the third container;

computing a true percent proof of the composition in the first container, the second container, or the third container based on the hydrometer reading and the temperature reading; and updating the composition of the first container, the second container, or the third container based on the true percent proof.

28. The method of claim 27, the method further comprising storing the true percent proof in a database.

29. The method of claim 27, the method further comprising: receiving a measured volume of the first container, the second container, or the third container;

computing a correction of the measured volume; and updating the composition of the first container, the second container, or the third container based on the correction of the measured volume.

30. The method of claim 29, the method further comprising storing the correction of the measured volume in a database.

31. The method of claim 25, wherein the distilled spirits in the third container are whiskey, blended whiskey with neutral spirits, blended whisky with light whiskey, blended light whiskey, imported scotch, imported Canadian whiskey, domestic whiskey distilled at 160 proof and under, domestic whiskey distilled at over 160 proof, brandy distilled at 170 proof and under, brandy distilled at over 170 proof, Puerto, Rican rum, Virgin Islands rum, domestic rum, gin, vodka, a cordial, a liquor, or tequila.

32. The method of claim 25, wherein the tracking step comprises obtaining a container equipment record from a database for each container in the plurality of containers.

33. The method of claim 32, wherein each the container equipment record is created at a time prior to the tracking step.

34. The method of claim 25, wherein the third container is a tank, barrel, mill, pot still, cast, storage silo, high column plate still, mash tub, or quashback.

35. The method of claim 25, wherein the third container is empty when the third quantity of the third distilled spirit is placed into the third container.

36. The method of claim 25, wherein the blending comprises obtaining a unit operation record that specifies the first quantity, the first container, the second quantity, and the second container.

37. The method of claim 36, wherein the unit operation record is stored in a database.

38. The method of claim 25, wherein the at least a first container is in a first plant and the at least a second container is in a second plant.

39. The method of claim 25, wherein the tracking step comprises periodically generating a report comprising any combination of:

(i) amounts of distilled spirits in the plurality of containers at a beginning of a period;
(ii) amounts received;
(iii) amounts dumped as alcohol flavor;
(iv) amounts mixed with wine;
(v) amounts dumped for further processing;
(vi) gains;
(vii) amounts bottled or packaged;
(viii) amounts withdrawn without payment of tax;
(ix) amounts withdrawn for research, development, or testing;
(x) amounts destroyed;
(xi) amounts used for redistillation;
(xii) amounts lost; and
(xiii) amounts on hand at the end of the end of said period.

40. The method of claim 39, wherein amounts are in quantities of proof gallons.

41. The method of claim 39, wherein amounts are reported separately for bulk ingredients and finished product.

42. The method of claim 39, wherein amounts are reported separately for each plant number or plant location that houses a container in the plurality of containers.

43. The method of claim 39, wherein the period is a day, week, month, or year.

44. The method of claim 39, wherein the report includes quantities of bulk spirits that have been dumped into processing, imported, bottled, bottled in bond, and bottled for export during the period.

45. The method of claim 44, wherein the quantities are itemized by:

(i) alcohol and neutral spirits other than vodka;
(ii) blended straight whiskey;
(iii) blended whiskey with neutral spirits;
(iv) blended whisky with light whiskey;
(v) blended light whiskey;
(vi) all other blends of 100% whiskey;
(vii) imported scotch;
(viii) imported Canadian whiskey;
(ix) domestic whiskey distilled at 160 proof and under;
(x) domestic whiskey distilled at over 160 proof;
(xi) brandy distilled at 170 proof and under;
(xii) brandy distilled at over 170 proof;
(xiii) Puerto Rican rum;
(xiv) Virgin Islands rum;
(xv) domestic rum;
(xvi) gin;
(xvii) vodka;
(xviii) cordial, liquors and specialties; and
(xiv) tequila.

46. The method of claim 25, further comprising displaying or outputting the composition and quantity of distilled spirits in the first container, the second container, and the third container, wherein outputting includes outputting to a user interface device, a monitor, a computer-readable storage medium, a computer-readable memory, or a local or remote computer system.

* * * * *